(12) United States Patent
Toscano et al.

(10) Patent No.: US 10,273,202 B2
(45) Date of Patent: Apr. 30, 2019

(54) NITROXYL PROGENITOR COMPOUNDS AND METHODS OF USE

(71) Applicants: John P. Toscano, Glen Arm, MD (US); Christopher M. Pavlos, Laurel, MD (US); Preeya Kapur Boppana, Frederick, MD (US)

(72) Inventors: John P. Toscano, Glen Arm, MD (US); Christopher M. Pavlos, Laurel, MD (US); Preeya Kapur Boppana, Frederick, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 14/492,741

(22) Filed: Sep. 22, 2014

(65) Prior Publication Data

US 2015/0141378 A1    May 21, 2015

Related U.S. Application Data

(63) Continuation of application No. 10/587,644, filed as application No. PCT/US2005/003183 on Jan. 28, 2005, now abandoned.

(60) Provisional application No. 60/632,456, filed on Dec. 2, 2004, provisional application No. 60/540,688, filed on Jan. 30, 2004.

(51) Int. Cl.
| | |
|---|---|
| *C07C 247/22* | (2006.01) |
| *C07C 291/08* | (2006.01) |
| *C07C 247/16* | (2006.01) |
| *C07C 247/18* | (2006.01) |
| *C07D 207/50* | (2006.01) |
| *C07D 209/42* | (2006.01) |

(52) U.S. Cl.
CPC .......... *C07C 247/16* (2013.01); *C07C 247/18* (2013.01); *C07C 291/08* (2013.01); *C07D 207/50* (2013.01); *C07D 209/42* (2013.01)

(58) Field of Classification Search
CPC ... C07C 247/16; C07C 247/18; C07C 247/22; C07C 291/08; C07D 207/50; C07D 209/50
USPC .................................................. 514/183, 590
See application file for complete search history.

(56) References Cited

U.S. PATENT DOCUMENTS

| | | |
|---|---|---|
| 4,954,526 A | 9/1990 | Keefer |
| 5,039,705 A | 8/1991 | Keefer et al. |
| 5,700,830 A | 12/1997 | Korthuis et al. |

(Continued)

FOREIGN PATENT DOCUMENTS

| | | |
|---|---|---|
| WO | 90009785 | 9/1990 |
| WO | WO 96/15781 A1 | 5/1996 |

(Continued)

OTHER PUBLICATIONS

Champion et al (J Urology, 1999; 161:2013-2019).*

(Continued)

*Primary Examiner* — Marcos L Sznaidman
*Assistant Examiner* — Rayna Rodriguez
(74) *Attorney, Agent, or Firm* — Byrne Poh LLP; Nina R. Horan

(57) ABSTRACT

Described herein are nitroxyl progenitor compounds, and compositions including, and methods or generating, the compounds thereof, and methods of treating or preventing disease and disease symptoms using the compounds and compositions.

4 Claims, 6 Drawing Sheets

Spectrophotometric Detection of HNO by Trapping with Methemoglobin $$Fe(III) + HNO \longrightarrow Fe(II)NO$$

characteristic absorption between 530 and 600 nm

NO can also give a small response:

But glutathione quenching can confirm HNO:

$$k_{HNO} = 2 \times 10^6 \ M^{-1}s^{-1}$$

$$k_{NO} < 4 \times 10^2 \ M^{-1}s^{-1}$$

*glutathione will quench the characteristic Fe(II)NO absorption between 530 and 600 nm if it was produced via reaction with HNO, but will not if it was produced via reaction with NO*

(56) References Cited

U.S. PATENT DOCUMENTS

| | | | |
|---|---|---|---|
| 5,958,427 | A | 9/1999 | Salzman et al. |
| 6,200,558 | B1 | 3/2001 | Saavedra et al. |
| 6,936,639 | B2 | 8/2005 | Wink et al. |
| 2004/0038947 | A1 | 2/2004 | Wink et al. |
| 2004/0158048 | A1 | 8/2004 | Ruane et al. |
| 2005/0009789 | A1 | 1/2005 | Wink et al. |

FOREIGN PATENT DOCUMENTS

| | | | |
|---|---|---|---|
| WO | WO 96/15797 | A1 | 5/1996 |
| WO | WO 98/19996 | A1 | 5/1998 |
| WO | WO 03/006427 | A1 | 1/2003 |
| WO | WO 03/080039 | A1 | 10/2003 |
| WO | WO 2005/074598 | | 8/2005 |

OTHER PUBLICATIONS

Office Action dated Nov. 24, 2014 in European Patent Application No. 05726388.1.
Bivalacqua, J. of Cardiovascular Pharm. 38(1):120-129 (2001).
Xiaoping, Tetrahedron Letters, 42:2625-2629 (2001).
Aloka, J. Am. Chem. Soc., 123:5465-5472 (2001).
Database CA [Online] XP002536112, Database Accession No. 2002:73572 (2002), abstract.
Database CA [Online] XP002536113, Database Accession No. 2001:253569 (2001), abstract.
Database CA [Online] XP002536114, Database Accession No. 1996:476772 (1996), abstract.
Database CA [Online] XP002536115, Database Accession No. 2001:178345, abstract.
Database CA [Online] XP002536116, Database Accession No. 2002:178244, abstract.
Supplementary European Search Report dated Jul. 21, 2009, for European Application No. 05726388.1.
Fitzhugh et al., "Qualitative Thin-Layer and High-Peformance Liquid Chromatographic Analysis of 1-Substituted Diazen-1-ium-1,2-diolates on Aminopropyl-Bonded Silica Gel," Anal. Biochem. 301(1):97-102 (2002).
Hortsmann et al., "Release of Nitric Oxide from Novel Diazeniumdiolates Monitored by Laser Magnetic Resonance Spectroscopy," Nitric Oxide 6(2):135-141 (2002).
International Search Report dated Nov. 1, 2005, for PCT Application No. PCT/US2005/003183.
Saavedra et al., "The Secondary Amine/Nitric Oxide Complex Ion $R_2N[N(0)NO]^-$ as Nucleophile and Leaving Group in $S_NAr$ Reactions," Journal of Organic Chemistry 66(9):3090-3098 (2001).
Vippagunta et al., "Crystalline solids," 2001, Advanced Drug Delivery Reviews, 48: 3-26.
Patani et al., "Bioisosterism: A Rational Approach in Drug Design," 1996, Chem. Rev. 96: 3147-3176.
Ismail, "Important fluorinated drugs in experimental and clinical use," 2002, Journal of Fluorine Chemistry, 118: 27-33.
Cao et al., "Nitric oxide inhibits uptake of dopamine and N-methyl-4-phenylpyridinium ($MPP^+$) but not release of $MPP^+$ in rat C6 glioma cells expressing human dopamine transporter," British Journal of Pharmacology, 137:1155-1162 (2002).
Hrabie et al., Chemistry of the Nitric Oxide-Releasing Diazeniumdiolate ("Nitrosohydroxylamine") Functional Group and Its Oxygen-Substituted Derivatives, Chem. Rev., 102:1135-1154 (2002).
Chen et al., "Discovery Pharmaceutics-Challenges and Opportunities," The AAPS Journal, 8(2):E402-E408 (2006).
Paolocci et al., "Nitroxyl anion exerts redox-sensitive positive cardiac inotropy in vivo by calcitonin gene-related peptide signaling," Proc. Natl. Acad. Sci. USA, 98(18):10463-10468 (2001).
Paolocci et al., "Positive inotropic and lusitropic effects of HNO/$NO^-$ in failing hearts: Independence from β-adrenergic signaling," Proc. Natl. Acad. Sci. USA, 100(9):5537-5542 (2003).
Serbulea, "Generation and reactions of nitroxyl (HNO) and nitric oxide and quantum mechanical investigation of nitroxide," Ph.D. Dissertation, University of California, Los Angeles, Chapter 1, 35 pages (2009).

* cited by examiner

Spectrophotometric Detection of HNO by Trapping with Methemoglobin $$\boxed{Fe(III) + HNO \longrightarrow Fe(II)NO}$$

*characteristic absorption between 530 and 600 nm*

NO can also give a small response:

$$Fe(III) + NO \rightleftharpoons Fe(III)NO$$

$$Fe(III)NO + H_2O \longrightarrow Fe(II) + NO_2^- + 2H^+$$

$$Fe(II) + NO \longrightarrow Fe(II)NO$$

But glutathione quenching can confirm HNO:

$$k_{HNO} = 2 \times 10^6 \, M^{-1} s^{-1}$$

$$k_{NO} < 4 \times 10^2 \, M^{-1} s^{-1}$$

*glutathione will quench the characteristic Fe(II)NO absorption between 530 and 600 nm if it was produced via reaction with HNO, but will not if it was produced via reaction with NO*

Figure 1.

NITROXYL PROGENITOR COMPOUNDS AND METHODS OF USE

CROSS-REFERENCE TO RELATED APPLICATIONS

This application is a continuation of application Ser. No. 10/587,644, filed Nov. 26, 2008, which is a national stage of application serial no. PCT/US05/03183, filed Jan. 28, 2005, which claims the benefit under 35 U.S.C. § 119(e) of provisional application Ser. No. 60/540,688, filed Jan. 30, 2004, and 60/632,456, filed Dec. 2, 2004, the contents of all of which are incorporated herein by reference.

GOVERNMENT SUPPORT

This work described herein was supported by a grant from the National Institutes of Health (Grant No. R01 GM-58109). Therefore, the U.S. Government may have certain rights in the invention.

BACKGROUND OF THE INVENTION

Compounds containing the diazeniumdiolate $[N(O)=NO]^-$ functional group have proven useful as research tools in a variety of applications requiring spontaneous release of nitric oxide (NO). Hrabie, J. A.; Keefer, L. K. *Chem. Rev.* 2002, 102, 1135-1154. Anions such as 1-(N,N-dialkylamino)diazen-1-ium-1,2-diolates 1 (where R is alkyl) are stable as solid salts, but release up to 2 mol of NO when dissolved in aqueous solution at physiologically relevant conditions.

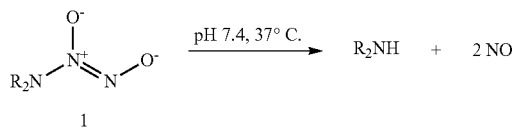

These compounds have shown great potential in a variety of medical applications requiring either the rapid production or gradual release of NO (see, Keefer, L. K. *Annu. Rev. Pharmacol. Toxicol.* 2003, 43, 585-607; Saavedra, J. E.; Fitzhugh, A. L.; Keefer, L. K. *Nitric Oxide and the Cardiovascular System* 2000, 431-446), and have allowed biological consequences of NO delivery rates to be probed. Saavedra, J. E.; Fitzhugh, A. L.; Keefer, L. K. *Nitric Oxide and the Cardiovascular System* 2000, 431-446.

A major factor affecting decomposition rate is ease of protonation at the amine nitrogen leading to amine and 2 equivalents of NO:

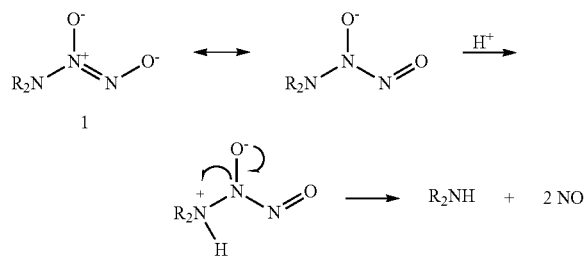

It is now discovered that by making protonation at this site unfavorable, an alternate decomposition pathway to nitrosamine and nitroxyl (NOIHNO) becomes available as illustrated below:

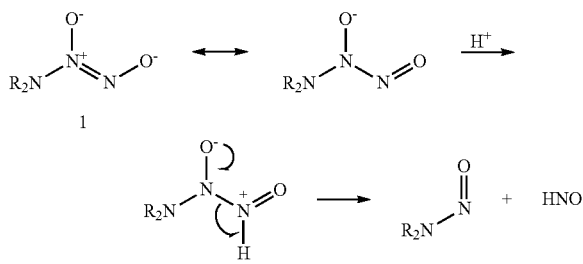

This has implications in that nitroxyl is implicated in the treatment of disease, including cardiovascular system diseases and disorders. Accordingly, as there is a need in the field for effective therapies for treating cardiovascular disorders, particularly by delivery of nitroxyl, the compounds herein and methods of using them provide unique and novel therapeutic opportunities.

SUMMARY OF THE INVENTION

Described herein are novel compounds, and compositions and methods of generating the compounds thereof, methods of providing nitroxyl and nitroxyl complexes, methods of treating disease and disease symptoms, and compounds useful for modulating nitroxyl levels for treating disease and disease symptoms.

One embodiment is a compound of formula (I), or pharmaceutically acceptable salt, solvate or hydrate thereof:

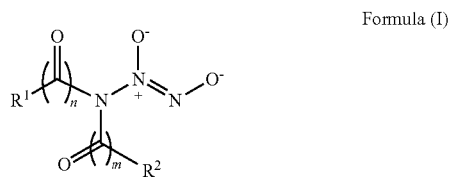

Formula (I)

wherein, each $R^1$ is H, alkyl, perhaloalkyl, cycloalkyl, cyclyl, aryl, heterocycloalkyl, heterocyclyl, heteroaryl, each optionally substituted with 1-4 groups that are halo, CN, $NO_2$, C(O)OH, C(O)OR, haloalkyl, or electron-withdrawing group;

each $R^2$ is alkyl, perhaloalkyl, cycloalkyl, cyclyl, aryl, heterocycloalkyl, heterocyclyl or heteroaryl, each optionally substituted with 1-4 groups that are halo, CN, $NO_2$, C(O)OH, C(O)OR, haloalkyl, or electron-withdrawing group;

or $R^1$ and $R^2$, together with the nitrogen to which they are both attached, is a heterocycloalkyl, heterocyclyl or heteroaryl ring optionally substituted with one or more groups that are halo, alkyl, C(O)OH, C(O)OR, haloalkyl;

each R is independently alkyl, alkenyl, alkynyl, cycloalkyl, cyclyl, aralkyl, or heteroaralkyl; and each n and m is independently 0 or 1.

Other embodiments are those of the formulae herein wherein: $R^2$ is a phenyl substituted with an electron-withdrawing group; wherein $R^1$ is alkyl; wherein $R^1$ is alkyl substituted with C(O)OH; wherein $R^1$ is independently a phenyl substituted with an electron-withdrawing group, and $R^2$ is independently a phenyl substituted with an electron-withdrawing group; wherein $R^1$ is independently alkyl optionally substituted with an electron-withdrawing group, and $R^2$ is independently a phenyl substituted with an electron-withdrawing group; wherein $R^2$ is a phenyl with a para-substituent, wherein the para-substituent is an electron-withdrawing group; wherein $R^1$ and $R^2$ taken together with the nitrogen to which they are both attached, is:

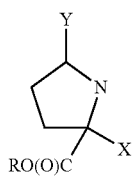
Formula (II)

wherein,
X is halo; and
Y is H or halo;

wherein $R^1$ is alkyl and $R^2$ is a phenyl with a para-substituent, wherein the para-substituent is an electron-withdrawing group; wherein $R^1$ is alkyl substituted with C(O)OH and $R^2$ is a phenyl with a para-substituent, wherein the para-substituent is an electron-withdrawing group; wherein both the carbon atom of $R^1$ attached to the nitroso nitrogen atom and the carbon atom of $R^2$ attached to the nitroso nitrogen atom are devoid of hydrogen substituents; wherein $R^1$ is independently a phenyl substituted with a 4-carboxy group, and $R^2$ is independently a phenyl substituted with a 4-carboxy group; wherein $R'$ is perfluoroalkyl; and m and n are each 0; wherein $R^1$ is $CF_3$ or $CF_2CF_3$; wherein n and m are both 1; wherein n and m are both 0; or wherein n is 0 and m is 1

Other embodiments are those of the formulae herein, wherein:
$R^1$ and $R^2$ taken together with the nitrogen to which they are both attached, is any of formulae (IV)-(VII):

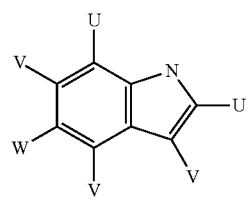
(IV)

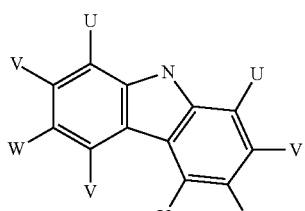
(V)

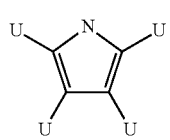
(VI)

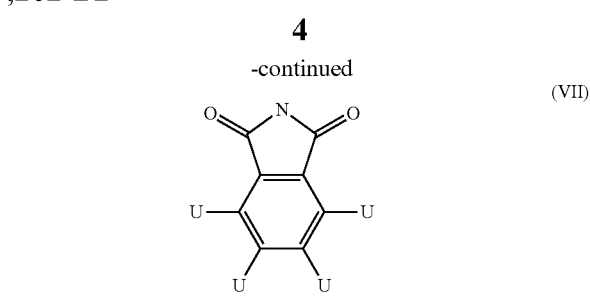
(VII)

wherein,
each U is independently H, alkyl, or an electron-withdrawing group;
each V is independently H or C(O)OH; and
each W is independently an electron-withdrawing group.

Other embodiments are those of the formulae herein, wherein:
$R^2$ is independently a group of formula (III):

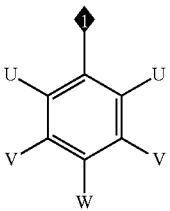
Formula (III)

wherein
each U is independently H, alkyl, or an electron-withdrawing group;
each V is independently H or C(O)OH; and
each W is independently an electron-withdrawing group.
each of $R^1$ and $R^2$ is independently a group of formula (III):

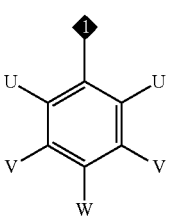
Formula (III)

wherein,
each U is independently H, alkyl, or an electron-withdrawing group;
each V is independently H or C(O)OH; and
each W is independently an electron-withdrawing group;
each $R^1$ is alkyl, cycloalkyl, cyclyl, aryl, heterocycloalkyl, heterocyclyl or heteroaryl, each optionally substituted with 1-4 groups that are halo, CN, $NO_2$, C(O)OH, C(O)OR, haloalkyl, or electron-withdrawing group; or
each $R^1$ is alkyl, cycloalkyl, cyclyl, aryl, heterocycloalkyl, heterocyclyl or heteroaryl, each substituted with 1-4 groups that are halo, CN, $NO_2$, C(O)OH, C(O)OR, haloalkyl, or electron-withdrawing group. Other embodiments are those wherein U and V are each H; or wherein one U is independently an electron-withdrawing group.

Another aspect is a compound of any of the formulae herein wherein independent $R^1$ and $R^2$ groups are those wherein the corresponding protonated amine form of the $R^1R^2N$— moiety (i.e., $R^1R^2NH_2+$) has a pKa of about 4.5 or less (e.g., about 4 or less, about 3 or less, about 2 or less, or about 1 or less).

Another aspect is a composition including a compound of any of the formulae herein and a pharmaceutically acceptable carrier. The composition can also include an additional therapeutic agent (e.g., cardiovascular agents). Additional cardiovascular agents include, for example, β-blockers β-antagonsists), calcium channel blockers, lipid lowering agents, cholesterol lowering agents (e.g., HMG CoA-reductase inhibitors), nitrates, angina agents, diuretics, angiotensin converting enzyme (ACE) inhibitors, angiotensin II receptor antagonists, vasodilators, antihypertensives and the like.

One aspect is a method of treating a subject suffering from or susceptible to a disease or disorder, or symptom thereof. The method includes the step of administering to the subject a therapeutic amount of a compound herein sufficient to treat the disease or disorder or symptom thereof under conditions such that the disease or disorder or symptom thereof is treated. In certain embodiments, the disease or disorder is a cardiovascular disease or disorder. In certain preferred embodiments, the subject is a human. In certain preferred embodiments, the subject is a subject identified as being in need of such treatment. In certain preferred embodiments, the subject is not suffering from a cancer. In certain embodiments, the method includes administration of an additional therapeutic agent. In certain preferred embodiments, the step of administering comprises administering the compound intravenously or intramuscularly.

In certain embodiments, the method further includes the step of determining a level of Marker in the subject. In certain embodiments, the step of determining of the level of Marker is performed prior to administration of the compound of the formulae hereinto the subject. In certain embodiments, the determining of the level of Marker is performed subsequent to administration of the compound of the formulae hereinto the subject. In certain embodiments, the determining of the level of Marker is performed prior to and subsequent to administration of the compound of the formulae hereinto the subject. In certain embodiments, the levels of Marker performed prior to and subsequent to administration of the compound of the formulae hereinto the subject are compared. In certain embodiments, the comparison of Marker levels is reported by a clinic, laboratory, or hospital agent to a health care professional. In certain embodiments, when the level of Marker performed prior to administration of the compound of the formulae hereinto the subject is lower or higher (depending on the Marker) than the level of Marker performed subsequent to administration of the compound of the formulae hereinto the subject, then the amount of compound administered to the subject is an effective amount.

In another aspect, an embodiment provides kits for treatment of a disease(s) or disorder(s) or symptoms thereof, including those of a cardiovascular nature. In one embodiment, the kit includes an effective amount of a compound of the formulae herein in unit dosage form, together with instructions for administering the compound of the formulae hereinto a subject suffering from or susceptible to a disease or disorder or symptoms thereof, including those of a cardiovascular nature. In preferred embodiments, the compound of the formulae herein is a nitroxyl progenitor.

In another aspect, an embodiment provides a method of treating a mammal to modulate nitroxyl levels (e.g., a method to administer nitroxyl to a subject), the method including administering to the mammal a therapeutically effective amount of at least one nitroxyl progenitor agent (e.g., a compound of any of the formulae herein) capable of providing nitroxyl. In other aspects, the methods are those wherein the mammal is in need of treatment for a condition that is associated nitroxyl mediation, including those delineated herein.

Another aspect is a method of modulating a target, including phospholamban (PLB), sarcolipin (SLN), skeletal or cardiac sarco(endo)plasmic reticulum calcium ATPase (SERCA), including isoforms thereof (e.g., SERCA2a, SERCA 1a), skeletal or cardiac sarcoplasmic reticulum (SR), or ryanodine receptors (RyR), in a cell comprising contacting a compound of any of the formulae herein with the cell such that the target is modulated. The method can also include modulating the target in a subject by administering the compound to the subject.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

Another aspect is a method of making a compound of any of the formulae herein, comprising taking a precursor compound (or intermediate) and reacting it with one or more chemical reagents to provide the compound of the formulae herein. The method can include one or more of the synthetic steps specifically delineated herein. Accordingly, another aspect is a compound made by a process delineated herein. The process can include one or more steps, reagents and starting materials as delineated herein using chemical reactions, techniques and protocols as delineated herein.

Another aspect is a method of making a pharmaceutical composition delineated herein, including the step of combining a compound herein (e.g., a compound of any of the formulae herein) with a pharmaceutically acceptable carrier. The method can further include combining an additional therapeutic agent with the compound and/or carrier.

Table 1 lists compounds (or salts or solvates thereof) that are representative embodiments of the formulae herein and are useful in the methods delineated herein.

TABLE 1

Nitroxyl Donor Compounds

TABLE 1-continued
Nitroxyl Donor Compounds
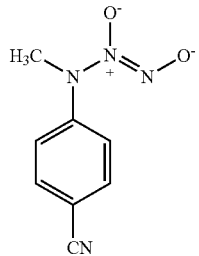
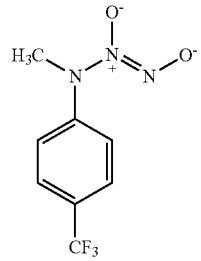
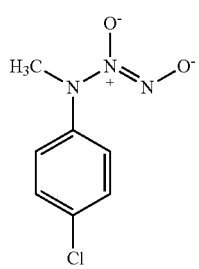
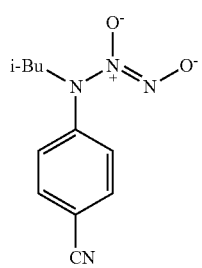
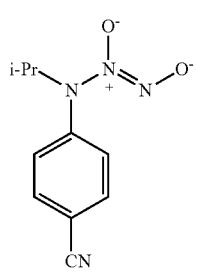
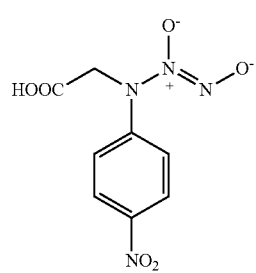
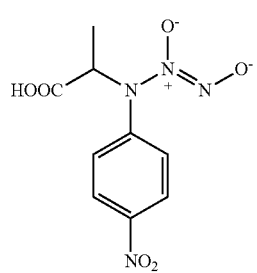
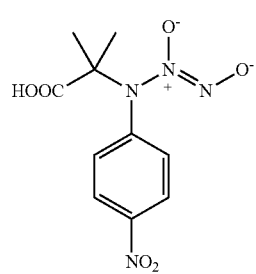
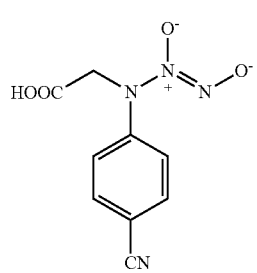
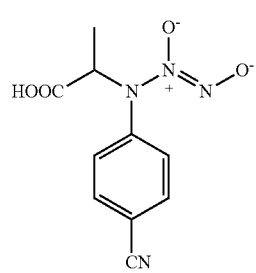

TABLE 1-continued

Nitroxyl Donor Compounds

[Chemical structures of nitroxyl donor compounds including F₃C and F₃CF₂C substituted diazeniumdiolate compounds with various aryl groups bearing COOH, NO₂, and CN substituents]

The compounds herein (and compound formulae herein) are depicted in their anionic form, however it is understood that the compound can be any corresponding salt form (e.g., sodium salt), that is the formulae herein having, for example, a counterion (e.g., M+) of appropriate charge wherein the M+ is a metal ion, for example, Na+, or a group Z, wherein Z is a photochemically cleavable, enzymatically cleavable, or hydrolytically cleavable functional group that upon exposure to photochemical, enzymatic or hydrolytic conditions, respectively, leads to cleavage of the Z group to provide the corresponding diazeniumdiolate. See, Hrabie, J. A.; Keefer, L. K. *Chem. Rev.* 2002, 102, 1135-1154; Ruane, P. H.; Bushan, K. M.; Pavlos, C. M.; D'Sa, R. A.; Toscano, J. P. *J. Am. Chem. Soc.;* 2002, 124(33), 9806-9811; Bushan, K. M.; Xu, H.; Ruane, P. 14; D'Sa, R. A.; Pavlos, C. M.; Smith, J. A.; Celius, T. C.; Toscano, J. P. *J. Am. Chem. Soc.* 2002, 124(43), 12640-12641.

BRIEF DESCRIPTION OF THE DRAWINGS

FIG. 1 describes spectrophotometric detection of HNO using methemoglobin.

DETAILED DESCRIPTION OF THE INVENTION

Figure 2:
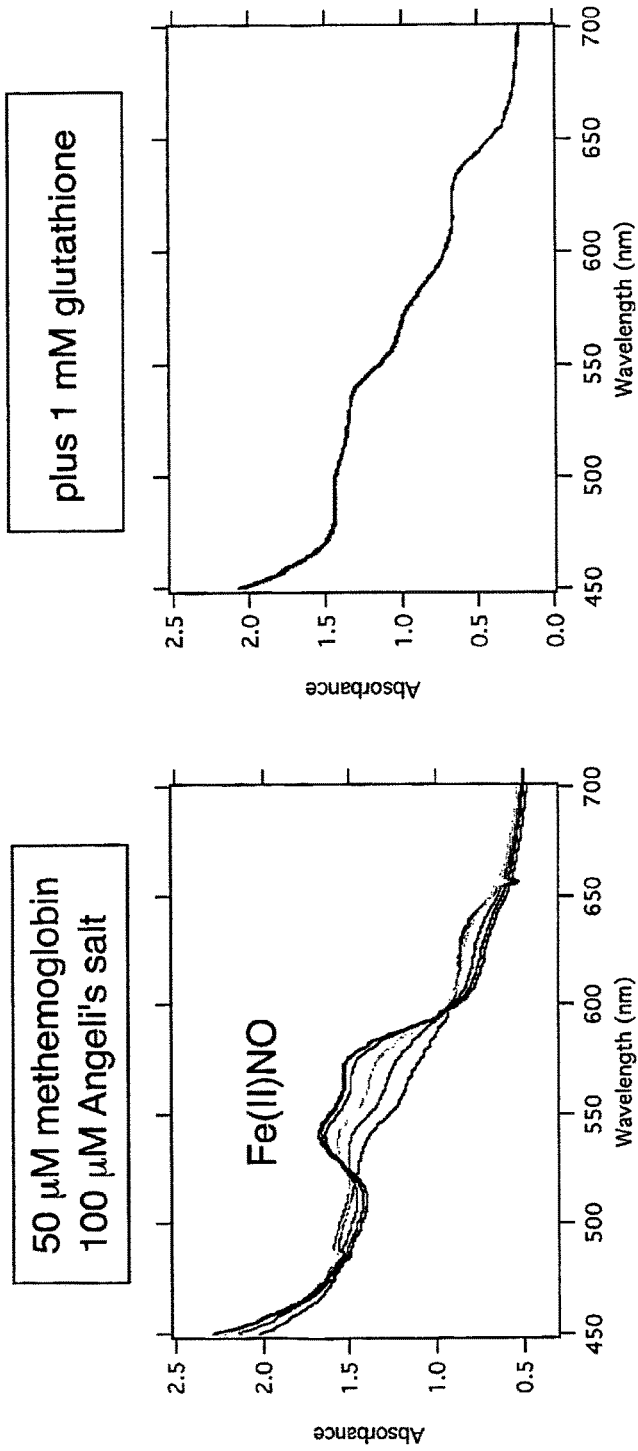
FIG. 2 illustrates results using Angeli's salt in methemoglobin assays.

Thus, completely different decomposition products for the related N-methylaniline derivatives 2 with X═H or CN are observed. For the parent compound 2 (X═H) the normal decomposition route provides amine and NO with a half-life of approximately 4 minutes at pH 7.4 and 37° C. With an electron-withdrawing substituent, however, protonation at the aniline nitrogen becomes very unfavorable and decomposition to nitrosamine and nitroxyl, with a half-life of approximately 12 minutes at pH 7.4 and 37° C., is observed for 2 (X═CN).

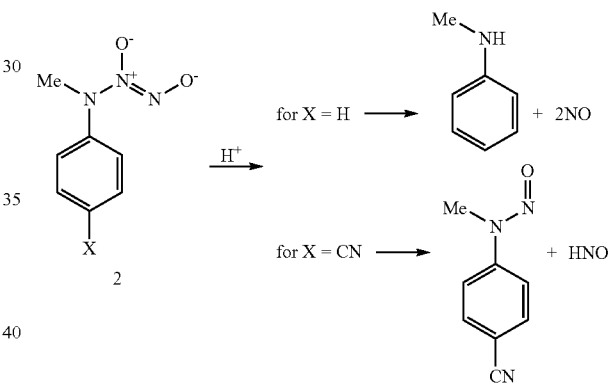

Each of these compounds was tested for their effects on cardiac function in canine models. In agreement with the observed products, 2 (X═H) behaves as an NO-donor, whereas 2 (X═CN) behaves as a nitroxyl-donor. Thus, compound 2 (X═CN) and analogous derivatives (described herein) have great potential in the treatment of disease, particularly nitroxyl-mediated disease including cardiovascular disease such as heart failure.

Another issue of note is related to the resulting nitrosamine by-product. Although certain nitrosamines are carcinogenic, the extent of carcinogenicity can be greatly reduced or eliminated by blocking sites for enzymatic hydroxylation, the key activation step leading to subsequent DNA alkylation (e.g., by substitution at the carbon alpha to the N-nitroso functionality) or by carboxylic acid (or other ionizable group (e.g., sulfonate)) substitution. Lijinsky, W. *Chemistry and Biology of N-Nitroso Compounds*, Cambridge University Press: Cambridge, UK, 1992. Thus, one embodiment provides for a compound of any of the formulae herein that provides a nitrosamine with reduced or no (as measured by an appropriate assay (e.g., Ames test; see, Kubo, T.; Urano, K.; Utsumi, H. "Mutagenicity Characteristics of 255 Environmental Chemicals," *J Health Sci* 2002, 48, 545-554; Oberly, T. J.; Hoffman, W. P.; Garriott, M. L.

"An Evaluation of the Twofold Rule for Assessing a Positive Response in the L5178y Tk+/− Mouse Lymphoma Assay," *Mutat Res-Genet Tox* 1996, 369, 221-232)) carcinogenicity; particularly wherein the $R^1$ and $R^2$ groups are those that provide a provide a nitrosamine with reduced or no carcinogenicity.

As used herein, the term "nitroxyl" refers to HNO or NO⁻ forms; and includes those forms that are derived from the nitroxyl progenitor or nitroxyl-donor compounds delineated herein (i.e., those compounds of the formulae herein).

As used herein, the terms 'cardiovascular disease' and 'cardiovascular disorder' refer to diseases and disorders, or symptoms thereof, of the cardiovascular system. Cardiovascular diseases/disorders include, but are not limited to, coronary obstructions, coronary artery disease (CAD), angina, heart attack, myocardial infarction, cardiac failure, high blood pressure, heart valve disease, and congestive heart failure. Related symptoms include shortness of breath, fatigue, swollen ankles or legs, angina, loss of appetite, weight gain or loss, associated with aforementioned diseases or disorders.

As noted, diseases, disorders or symptoms thereof of specific interest include those associated with nitroxyl or wherein nitroxyl may be implicated. Specifically, nitroxyl-mediated disorders include cardiovascular disorders, including, heart failure, including early-stage chronic heart failure, Class II heart failure, and hypertension; inflammation including diseases, disorders, or symptoms thereof that respond favorably to inhibition of cyclooxygenase (e.g., COX-2) activity (e.g., arthritis, joint pain) (see, Wink et al. US 2005/0009789); diseases, disorders or symptoms thereof involving inhibition of aldehyde dehydrogenase activity (e.g., treatment of alcoholism) (see, Conway, et al. *J. Med. Chem.* (1998) 41, 2903-2909; Shoeman et al. *Alcohol*, (2000) 20, 55-59; Niederhofer et al. *Alcohol and Alcoholism* (2003) 38, 50-53); conditions that respond favorably to attenuation of N-methyl-D-aspartate (NMDA) receptors (see, Kim et al. *Neuron* (1999), 24, 461-469); neurotransmission disorders; blood clotting; and immune-system control processes.

II. Compounds

Another embodiment is a method of making a compound of any of the formulae herein using any one, or combination of, reactions delineated herein. The method can include the use of one or more intermediates or chemical reagents delineated herein.

Another aspect is a radiolabeled compound of any of the formulae delineated herein. Such compounds have one or more radioactive atoms (e.g., $^3H$, $^2H$, $^{14}C$, $^{13}C$, $^{35}S$, $^{125}I$) introduced into the compound. Such compounds are useful for drug metabolism studies and diagnostics.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical. The term "ester" refers to a —C(O)O—R, wherein R is as defined herein. An "amido" is an —C(O)NH₂, and an "N-alkyl-substituted amido" is of the formula C(0)NHR, wherein R is as defined herein.

The term "mercapto" refers to a —SH group.

As used herein, the term "halogen" or "halo" means —F, —Cl, —Br or —I.

As used herein, the term "haloalkyl" means and alkyl group in which one or more (including all) the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, difluoromethyl, bromomethyl, 1,2-dichloroethyl, 4-iodobutyl, 2-fluoropentyl, and the like. The term "perhaloalkyl" refers to a alkyl group in which all hydrogen atoms are replaced by a halo group (e.g., trifluoromethyl, pentafluoroethyl).

The term "cycloalkyl" refers to a hydrocarbon 3-8 membered monocyclic or 7-14 membered bicyclic ring system having at least one non-aromatic ring. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclooctyl, cyclononyl, and cyclodecyl.

The term "cyclyl" refers to a hydrocarbon 3-8 membered monocyclic or 7-14 membered bicyclic ring system having at least one non-aromatic ring, wherein the non-aromatic ring has some degree of unsaturation. Cyclyl groups may be optionally substituted with one or more substituents. In one embodiment, 0, 1, 2, 3, or 4 atoms of each ring of a cyclyl group may be substituted by a substituent. Examples of cyclyl groups include cyclohexenyl, bicyclo[2.2.1]hept-2-enyl, dihydronaphthalenyl, benzocyclopentyl, cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

As used herein, the term "aralkyl" means an aryl group that is attached to another group by a (C1-C6)alkylene group. Aralkyl groups may be optionally substituted, either on the aryl portion of the aralkyl group or on the alkylene portion of the aralkyl group, with one or more substituent. Representative aralkyl groups include benzyl, 2-phenylethyl, naphth-3-yl-methyl and the like.

As used herein, the term "alkylene" refers to an alkyl group that has two points of attachment. The term "($C_1$-$C_6$) alkylene" refers to an alkylene group that has from one to six carbon atoms. Non-limiting examples of alkylene groups include methylene (—CH$_2$—), ethylene (—CH$_2$CH$_2$—), n-propylene (—CH$_2$CH$_2$CH$_2$—), isopropylene (—CH$_2$CH(CH$_3$)—), and the like.

The term "arylalkoxy" refers to an alkoxy substituted with aryl.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, 1-oxo-pyridyl, furanyl, benzo[1,3]dioxolyl, benzo[1,4]clioxinyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, and benzo(b)thienyl, 3H-thiazolo[2,3-c][1,2,4]thiadiazolyl, imidazo[1,2-d]-1,2,4-thiadiazolyl, imidazo[2,1-b]-1,3,4-thiadiazolyl, 1H,2H-furo[3,4-d]-1,2,3-thiadiazolyl, 1H-pyrazolo[5,1-c]-1,2,4-triazolyl, pyrrolo[3,4-d]-1,2,3-triazolyl, cyclopentatriazolyl, 31-I-pyrrolo[$^{3,4}$-c]isoxazolyl, 111,3H-pyrrolo[1,2-c]oxazolyl, pyrrolo[2,1b]oxazolyl, and the like.

As used herein, the term "heteroaralkyl" or "heteroarylalkyl" means a heteroaryl group that is attached to another group by a (C1-C6)alkylene. Heteroaralkyl groups may be optionally substituted, either on the heteroaryl portion of the heteroaralkyl group or on the alkylene portion of the heteroaralkyl group, with one or more substituent. Representative heteroaralkyl groups include 2-(pyridin-4-yl)-propyl, 2-(thien-3-yl)-ethyl, imidazol-4-yl-methyl and the like.

The term "heterocycloalkyl" refers to a nonaromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, 2-oxopiperazinyl, 2-oxopiperidinyl, 2-oxopyrrolidinyl, 4-piperidonyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane, tetrahydrofuranyl, tetrahydrothienyl, thiirene.

The term "heterocyclyl" refers to a nonaromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system has some degree of unsaturation. Heterocyclyl groups may be optionally substituted with one or more substituents. In one embodiment, 0, 1, 2, 3, or 4 atoms of each ring of a heterocyclyl group may be substituted by a substituent. Examples of these groups include thiirenyl, thiadiazirinyl, dioxazolyl, 1,3-oxathiolyl, 1,3-dioxolyl, 1,3-dithiolyl, oxathiazinyl, dioxazinyl, dithiazinyl, oxadiazinyl, thiadiazinyl, oxazinyl, thiazinyl, 1,4-oxathiin,1,4-dioxin, 1,4-dithiin, IH-pyranyl, oxathiepinyl, 5H-1,4-dioxepinyl, 5H-1,4-dithiepinyl, 6H-isoxazolo[2,3-d]1,2,4-oxadiazolyl, 7aH-oxazolo[3,2-d]1,2,4-oxadiazolyl, and the like.

The term "alkylamino" refers to an amino substituent which is further substituted with one or two alkyl groups. The term "aminoalkyl" refers to an alkyl substituent which is further substituted with one or more amino groups. The term "mercaptoalkyl" refers to an alkyl substituent which is further substituted with one or more mercapto groups. The term "hydroxyalkyl" refers to an alkyl substituent which is further substituted with one or more hydroxyl groups. The term "sulfonylalkyl" refers to an alkyl substituent which is further substituted with one or more sulfonyl groups. The term "sulfonylaryl" refers to an aryl substituent which is further substituted with one or more sulfonyl groups. The term alkylcarbonyl refers to an —C(O)-alkyl. The term "mercaptoalkoxy" refers to an alkoxy substituent which is further substituted with one or more mercapto groups.

The term "alkylcarbonylalkyl" refers to an alkyl substituent which is further substituted with —C(O)-alkyl. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions. Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

As used herein the term "substituent" or "substituted" means that a hydrogen radical on a compound or group (such as, for example, alkyl, alkenyl, alkynyl, alkylene, aryl, aralkyl, heteroaryl, heteroaralkyl, cycloalkyl, cyclyl, heterocycloalkyl, or heterocyclyl group) is replaced with any desired group that do not substantially adversely affect the stability of the compound. In one embodiment, desired substituents are those which do not adversely affect the activity of a compound. The term "substituted" refers to one or more substituents (which may be the same or different), each replacing a hydrogen atom. Examples of substituents include, but are not limited to, halogen (F, Cl, Br, or I), hydroxyl, amino, alkylamino, arylamino, dialkylamino, diarylamino, cyano, nitro, mercapto, oxo (i.e., carbonyl), thio, imino, formyl, carbamido, carbamyl, carboxyl, thioureido, thiocyanato, sulfoamido, sulfonylalkyl, sulfonylaryl, alkyl, alkenyl, alkoxy, mercaptoalkoxy, aryl, heteroaryl, cyclyl, heterocyclyl, wherein alkyl, alkenyl, alkyloxy, aryl, heteroaryl, cyclyl, and heterocyclyl are optionally substituted with alkyl, aryl, heteroaryl, halogen, hydroxyl, amino, mercapto, cyano, nitro, oxo (=O), thioxo (=S), or imino (=NR), wherein R is as defined herein.

In other embodiments, substituents on any group (such as, for example, alkyl, alkenyl, alkynyl, aryl, aralkyl, heteroaryl, heteroaralkyl, cycloalkyl, cyclyl, heterocycloalkyl, and heterocyclyl) can be at any atom of that group, wherein any group that can be substituted (such as, for example, alkyl, alkenyl, alkynyl, aryl, aralkyl, heteroaryl, heteroaralkyl, cycloalkyl, cyclyl, heterocycloalkyl, and heterocyclyl) can be optionally substituted with one or more substituents (which may be the same or different), each replacing a hydrogen atom. Examples of suitable substituents include, but not limited to alkyl, alkenyl, alkynyl, cyclyl, cycloalkyl, heterocyclyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, or alkoxycarbonylamino; alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Additional suitable substituents on alkyl, alkenyl, alkynyl, aryl, aralkyl, heteroaryl, heteroaralkyl, cycloalkyl, cyclyl, heterocycloalkyl, and heterocyclyl include, without limitation halogen, CN, $NO_2$, $OR^{15}$, $SR^{15}$, $S(O)_2OR^{15}$, $NR^{15}$, $C_1$-$C_2$ perfluoroalkyl, $C_1$-$C_2$ perfluoroalkoxy, 1,2-methylenedioxy, (=O), (=S), (=$NR^{15}$), $C(O)OR^{15}$, $C(O)NR^{15}R^{16}$, $OC(O)NR^{15}R^{16}$, $NR^{15}C(O)NR^{15}R^{16}$, $C(NR^{16})NR^{15}R^{16}$, $NR^{15}C(NR^{16})NR^{15}R^{16}$, $S(O)_2NR^{15}R^{16}$, $R^{17}$, $C(O)H$, $C(O)R^{17}$, $NR^{15}C(O)R^{17}$, $Si(R^{15})_3$, $OSi(R^{15})_3$, $Si(OH)_2R^{15}$, $B(OH)_2$, $P(O)(OR^{15})_2$, $S(O)R^{17}$, or $S(O)_2R^{17}$. Each $R^{15}$ is independently hydrogen, $C_1$-$C_6$ alkyl optionally substituted with cycloalkyl, aryl, heterocyclyl, or heteroaryl. Each $R^{16}$ is independently hydrogen, $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl. Each $R^{17}$ is independently $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl. Each $C_3$-$C_6$ cycloalkyl, aryl, heterocyclyl, heteroaryl and $C_1$-$C_4$ alkyl in each $R^{15}$, $R^{16}$ and $R^{17}$ can optionally be substituted with halogen, CN, $C_1$-$C_4$ alkyl, OH, $C_1$-$C_4$ alkoxy, COOH, $C(O)O$ $C_1$-$C_4$ alkyl, $NH_2$, $C_1$-$C_4$ alkylamino, or $C_1$-$C_4$ dialkylamino.

Substituents can also be "electron-withdrawing groups", that is, groups that reduce electron density of the moiety to which they are attached (relative to the density of the moiety without the substituent). Such groups include, for example, $NO_2$, $^+NR_3$, $SO_3H$, $S(O)_2R$, $C(O)OH$, $C(O)OR$, $C(O)R$, $C(O)H$, CN, $CF_3$ (where R is as defined herein) and the like.

As used herein, the term "lower" refers to a group having up to six atoms. For example, a "lower alkyl" refers to an alkyl radical having from 1 to 6 carbon atoms, and a "lower alkenyl" or "lower alkynyl" refers to an alkenyl or alkynyl radical having from 2 to 6 carbon atoms, respectively.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., formulation into therapeutic products, intermediates for use in production of therapeutic compounds, isolatable or storable intermediate compounds, treating diseases, disorders, or symptoms thereof, including those delineated herein). The compounds produced by the methods herein can be incorporated into compositions, including solutions, capsules, cremes, or ointments for administration to a subject (e.g., human, animal). Such compositions (e.g., pharmaceuticals) are useful for providing to the subject desirable health or other physiological benefits that are associated with such compounds.

The compounds of the formulae herein are available from commercial sources or may be synthesized using reagents and techniques known in the art, including those delineated herein. The chemicals used in the synthetic routes may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in R. Larock, *Comprehensive Organic Transformations*, VCH Publishers (1989); T. W. Greene and P. G. M. Wuts, Protective Groups in Organic Synthesis, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Nucleophilic agents are known in the art and are described in the chemical texts and treatises referred to herein. The chemicals used in the aforementioned methods may include, for example, solvents, reagents, catalysts, protecting group and deprotecting group reagents and the like. The methods described above may also additionally include steps, either before or after the steps described specifically herein, to add or remove suitable protecting groups in order to ultimately allow synthesis of the compound of the formulae described herein. The methods delineated herein contemplate converting compounds of one formula to compounds of another formula. The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Intermediates can be used with or without purification (e.g., filtration, distillation, crystallization, chromatography). Other embodiments relate to the intermediate compounds delineated herein, and their use in the methods (e.g., treatment, synthesis) delineated herein.

The compounds of this invention include the compounds themselves, as well as their salts, solvate, hydrate, polymorph, or prodrugs, if applicable. As used herein, the term "pharmaceutically acceptable salt," is a salt formed from, for example, an acid and a basic group of a compound of any one of the formulae disclosed herein. Illustrative salts include, but are not limited, to sulfate, citrate, acetate, chloride, bromide, iodide, nitrate, bisulfate, phosphate, acid phosphate, lactate, salicylate, acid citrate, tartrate, oleate, tannate, pantothenate, bitartrate, ascorbate, succinate, maleate, besylate, fumarate, gluconate, glucaronate, saccharate, formate, benzoate, glutamate, methanesulfonate, ethanesulfonate, benzenesulfonate, and p-toluenesulfonate salts. The term "pharmaceutically acceptable salt" also refers to a salt prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N, N-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound of any one of the formulae disclosed herein having a basic functional group, such as an amino functional group, and a pharmaceutically acceptable inorganic or organic acid. Suitable acids include hydrogen sulfate, citric acid, acetic acid, hydrochloric acid (BC!), hydrogen bromide (HBr), hydrogen iodide (HI), nitric acid, phosphoric acid, lactic acid, salicylic acid, tartaric acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

As used herein, the term "hydrate" means a compound of the present invention or a salt thereof, which further includes a stoichiometric or non-stoichiometric amount of water bound by non-covalent intermolecular forces.

III. Methods of Treatment

In one embodiment, the present invention provides methods of treating disease and/or disorders or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to a cardiovascular disease or disorder or symptom thereof. The method includes the step of administering to the mammal a therapeutic amount of an amount of a compound herein sufficient to treat the disease or disorder or symptom thereof, under conditions such that the disease or disorder is treated.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The preferred therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a cardiovascular disease, disorder, or symptom thereof. The nitroxyl progenitor compounds herein may be also used in the treatment of any other disorders in which nitroxyl may be implicated.

For therapeutic applications, the compounds of the formulae herein may be suitably administered to a subject such as a mammal, particularly a human, alone or as part of a pharmaceutical composition, comprising the formulae herein together with one or more acceptable carriers thereof and optionally other therapeutic ingredients. The carrier(s) must be "acceptable" in the sense of being compatible with the other ingredients of the formulation and not deleterious to the recipient thereof.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets and sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier which constitutes one or more accessory ingredients. In general, the compositions are prepared by uniformly and intimately bringing into association the active ingredients with liquid carriers, liposomes or finely divided solid carriers or both, and then if necessary shaping the product.

In certain preferred embodiments, the compound is administered orally. Compositions of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein. Methods of formulating such slow or controlled release compositions of pharmaceutically active ingredients, such as those herein and other compounds known in the art, are known in the art and described in several issued US patents, some of which include, but are not limited to, U.S. Pat. Nos. 4,369,172; and 4,842,866, and references cited therein. Coatings can be used for delivery of compounds to the intestine (see, e.g., U.S. Pat. Nos. 6,638,534, 5,217,720, and 6,569,457, and references cited therein).

A skilled artisan will recognize that in addition to tablets, other dosage forms can be formulated to provide slow or controlled release of the active ingredient. Such dosage forms include, but are not limited to, capsules, granulations and gel-caps.

Compositions suitable for topical administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access. Where an organ or tissue is accessible because of removal from the patient, such organ or tissue may be bathed in a medium containing the subject compositions, the subject compositions may be painted onto the organ, or may be applied in any convenient way.

As used herein, the terms "nitroxyl progenitor" and "nitroxyl donor" compound (including those of the formulae delineated herein) include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) an active compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group which enhances aqueous solubility or active transport through the gut membrane is appended to the structure of formulae described herein. See, e.g., Alexander, J. et al. *Journal of Medicinal Chemistry* 1988, 31, 318-322; Bundgaard, H. *Design of Prodrugs*; Elsevier: Amsterdam, 1985; pp 1-92; Bundgaard, H.; Nielsen, N. M. *Journal of Medicinal Chemistry* 1987, 30, 451-454; Bundgaard, H. *A Textbook of Drug Design and Development*; Harwood Academic Publ.: Switzerland, 1991; pp 113-191; Digenis, G. A. et al. *Handbook of Experimental Pharmacology* 1975, 28, 86-112; Friis, G. J.; Bundgaard, H. *A Textbook of Drug Design and Development;* 2 ed.; Overseas Publ.: Amsterdam, 1996; pp 351-385; Pitman, I. H. *Medicinal Research Reviews* 1981, 1, 189-214.

The compounds of this invention may be modified by appending appropriate functionalities to enhance selective biological properties. Such modifications are known in the art and include those which increase biological penetration into a given biological compartment (e.g., central nervous system), increase oral availability, increase solubility to allow administration by injection, alter metabolism and alter rate of excretion. It will be appreciated that actual preferred amounts of a given nitroxyl modulator of the invention used in a given therapy will vary according to the particular active compound being utilized, the particular compositions formulated, the mode of application, the particular site of administration, the patient's weight, general health, sex, etc., the particular indication being treated, etc. and other such factors that are recognized by those skilled in the art including the attendant physician or veterinarian. Optimal administration rates for a given protocol of administration can be readily determined by those skilled in the art using conventional dosage determination tests, or by any method known in the art or disclosed herein.

The compounds herein may contain one or more asymmetric centers and thus occur as racemates and racemic mixtures, single enantiomers, individual diastereomers and diastereomeric mixtures. All such isomeric forms of these compounds are expressly included in the present invention. The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented (e.g., alkylation of a ring system may result in alkylation at multiple sites, the invention expressly includes all such reaction products). All such isomeric forms of such compounds herein are expressly included in the present invention. All crystal forms and polymorphs of the compounds described herein are expressly included in the present invention. The term "N-oxides" refers to one or more nitrogen atoms, when present in an aromatic ring nitrogen-containing compound, that are in N-oxide oxidation form, i.e., N→O.

In certain method embodiments, a level of Marker or Marker activity in a subject is determined at least once. Comparison of Marker levels, e.g., to another measurement of Marker level obtained previously or subsequently from the same patient, another patient, or a normal subject, may be useful in determining whether therapy according to the invention is having the desired effect, and thereby permitting adjustment of dosage levels as appropriate. Determination of Marker levels may be performed using any suitable sampling/expression assay method known in the art or described herein. Preferably, a tissue or fluid sample is first removed from a subject. Examples of suitable samples include blood, mouth or cheek cells, and hair samples containing roots. Other suitable samples would be known to the person skilled in the art. Determination of protein levels and/or mRNA levels (e.g., Marker levels) in the sample can be performed using any suitable technique known in the art, including, but not limited to, enzyme immunoassay, ELISA, radiolabelling/assay techniques, blotting/chemiluminescence methods, real-time PCR, and the like.

Therefore, in certain embodiments, compounds of the invention, such as those of the formulae herein, are administered at dosage levels of about 0.0001 to 4.0 grams once per day (or multiple doses per day in divided doses) for adults. Thus, in certain embodiments of this invention, a compound herein is administered at a dosage of any dosage range in which the low end of the range is any amount between 0.1 mg/day and 400 mg/day and the upper end of the range is any amount between 1 mg/day and 4000 mg/day (e.g., 5 mg/day and 100 mg/day, 150 mg/day and 500 mg/day). In other embodiments, a compound herein, is administered at a dosage of any dosage range in which the low end of the range is any amount between 0.1 mg/kg/day and 90 mg/kg/day and the upper end of the range is any amount between I mg/kg/day and 100 mg/kg/day (e.g., 0.5 mg/kg/day and 2 mg/kg/day, 5 mg/kg/day and 20 mg/kg/day). The dosing interval can be adjusted according to the needs of individual patients. For longer intervals of administration, extended release or depot formulations can be used.

In one embodiment, the invention provides a method of monitoring treatment progress. The method includes the step of determining a level of diagnostic marker (Marker) (e.g., creatine kinase or isoenzymes thereof, e.g., CK-MB, troponins, e.g., troponin 1, T or C, myoglobin, myosin, or any target delineated herein modulated by nitroxyl or a compound herein) or diagnostic measurement (e.g., electrocardiogram (EKG), blood pressure, stress test) in a subject suffering from or susceptible to a disorder or symptoms thereof associated with cardiovascular disease, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

In other method embodiments, the levels of metabolites from the nitroxyl progenitor compounds can assessed. For example, the methods can further include assessment of levels of nitroxyl or nitrosamine (or metabolites thereof) resulting from the nitroxyl progenitor compounds. Parameters such as the subject identification or selection for the treatment regimen, treatment efficacy, treatment protocol status or dosage range can be determined using these measurements.

IV. Kits

The invention also provides kits for treatment or prevention of a disease or disorder (or symptoms) thereof, including a cardiovascular disease, disorder or symptom thereof. In one embodiment, the kit includes an effective amount of a compound herein in unit dosage form, together with instructions for administering the compound to a subject suffering from or susceptible to a disease or disorder or symptoms thereof. In other embodiments, the kit comprises a sterile container which contains the compound; such containers can be boxes, ampules, bottles, vials, tubes, bags, pouches, blister-packs, or other suitable container form known in the art. Such containers can be made of plastic, glass, laminated paper, metal foil, or other materials suitable for holding medicaments. The instructions will generally include information about the use of the compound of the formulae herein for treatment of a disease or disorder or symptoms thereof, including those of a cardiovascular nature. In other embodiments, the instructions include at least one of the following: description of the compound; dosage schedule and administration for treatment of a disease or disorder or symptoms thereof, including those of a cardiovascular nature; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The invention will be further described in the following examples. It should be understood that these examples are for illustrative purposes only and are not to be construed as limiting this invention in any manner.

EXAMPLES

Example 1

Synthetic Procedure:

Compounds 2 were prepared by treating a solution of the appropriate N-methylaniline derivative (1 g) in methanol (5 mL) with one equivalent of sodium methoxide (25% w/w in methanol) in a standard Parr hydrogenation bottle. The reaction vessel was purged with nitrogen and then saturated with excess NO. The reaction was allowed to stir at room temperature for 48 hours during which time the pressure of NO gas was maintained at approximately 40 psi. The product was isolated by filtration and washed with ethyl ether and dried under vacuum. The spectroscopic/physicochemical properties of the products obtained were consistent with the desired products. Other compounds delineated herein can be made similarly using the respective appropriate starting materials.

Determination of Decomposition Products:

Half-lives were determined by UV-Vis spectroscopy at 37° C. in pH 7.4 phosphate buffer. The decomposition products of compounds 2 were examined at 37° C. and pH 7.4. Organic products (the corresponding amines and nitrosamines) were characterized by UV-Vis, and NMR analysis, and quantified by HPLC analysis. NO was detected electrochemically using an inNO Measuring System with an amiNO-700 probe (Innovative Instruments). HNO was measured by trapping with methemoglobin as has been described in the literature. (See, Addison, A. W.; Stephanos, J. J. *Biochemistry* 1986, 25, 4104-4113; Bazylinkski, D. A.; Hollocher, T. C. *J. Am. Chem. Soc.* 1985, 107, 7982-7986.) The reactions of both I-INO and NO with methemoglobin, and the effects of added glutathione are detailed in FIG. 1. As shown in Table A, the results indicate that the decomposition products are strongly dependent on the para-substituent X.

Figure 3:
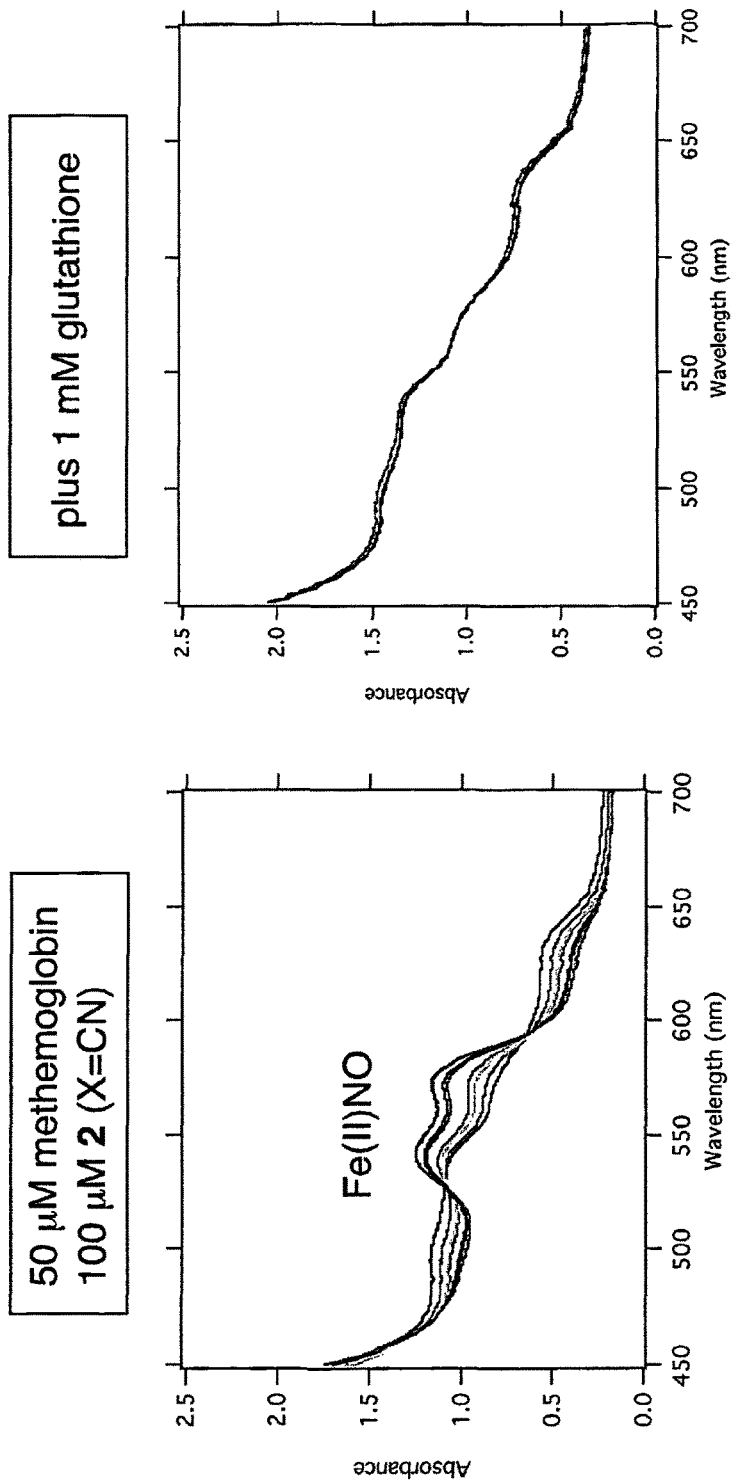
FIG. 3 illustrates results using test compound in methemoglobin assays.
Figure 4:
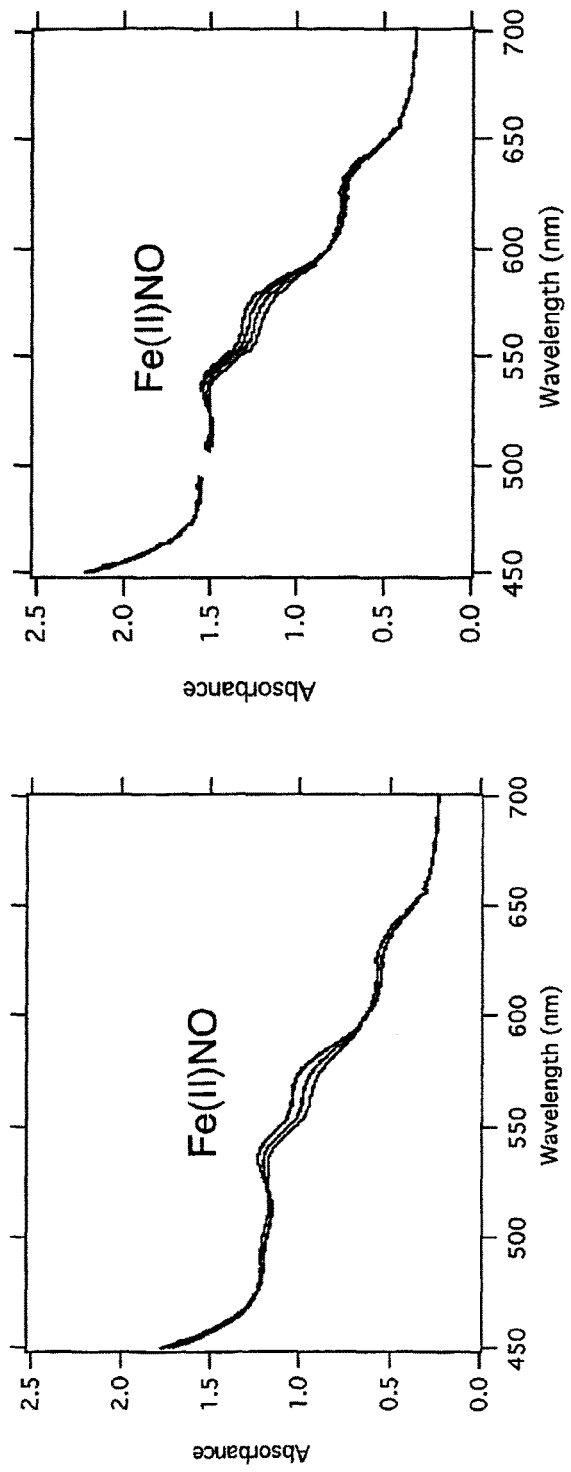
FIG. 4 illustrates results using test compound in methemoglobin assays.
Figure 5:
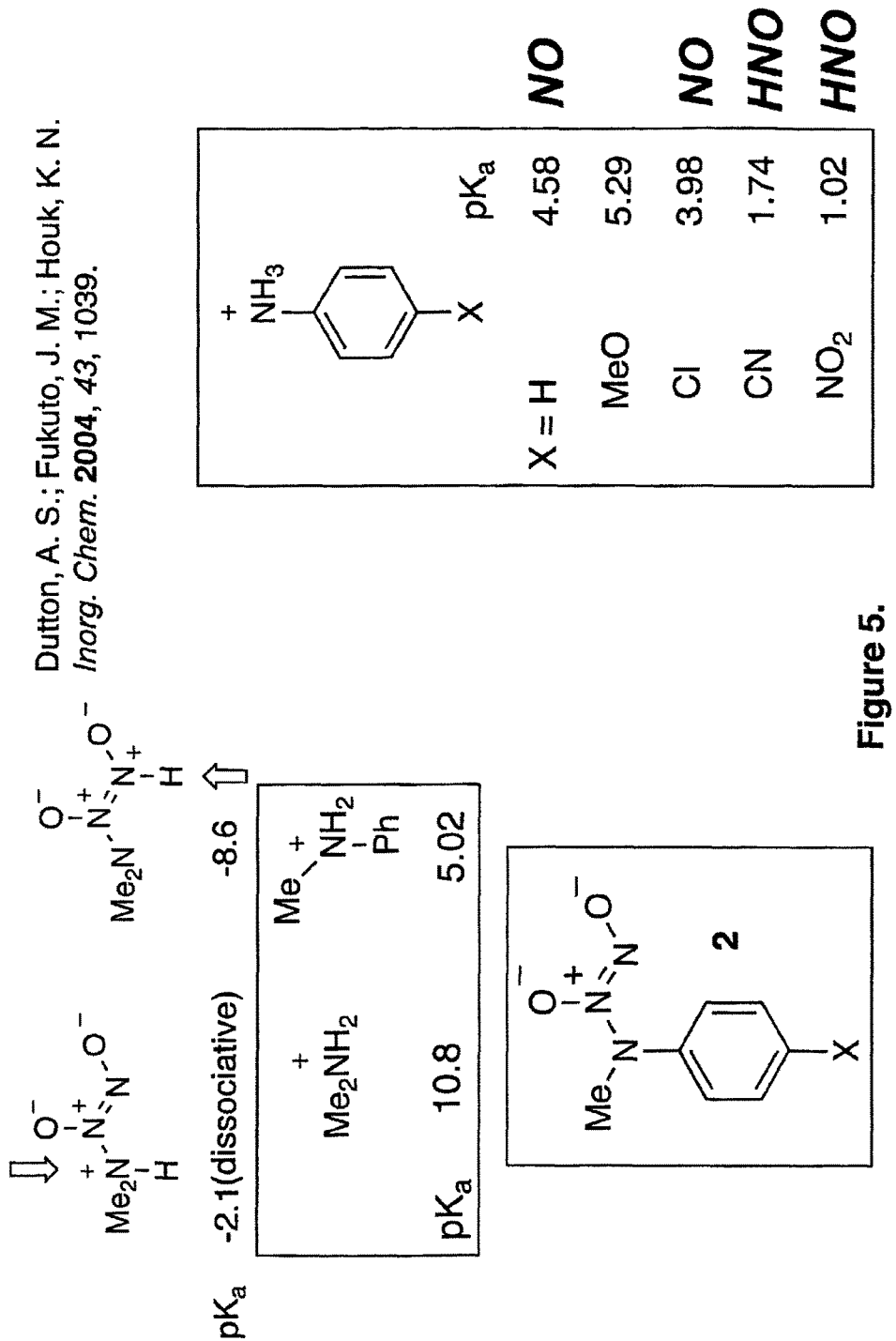
FIG. 5 illustrates the effect of pKa of the protonated form of the corresponding amine moiety of the compounds of the formulae herein.

As shown in FIG. 2, when deaerated solutions of methemoglobin (50 μM) are treated with 100 μM Angeli's salt (AS), a classic nitroxyl donor, a distinct absorption band due to the iron-nitrosyl (Fe(II)NO) complex is observed between 530 and 600 nm. When the experiment is repeated in the presence of 1 mM glutathione, the absorption band due to the iron-nitrosyl is completely quenched, indicating that all the HNO produced from AS is scavenged. Analogous experiments with HNO donor 2 (X=CN) gives similar results (see FIG. 3), but those with NO donor 2 (X=H) do not (see FIG. 4). As shown in FIG. 1, NO does react slowly with methemoglobin to give a small amount of iron-nitrosyl. However, NO is not quenched as rapidly by glutathione as is HNO; thus when the experiment is repeated in the presence of 1 mM glutathione, the weak signal is still observed (FIG. 4). In addition, the presence of $N_2O$ (the product of HNO dimerization and subsequent dehydration) was assayed by gas chromatography. FIG. 5 provides a summary of the results obtained and the effect of the $pK_a$ of the protonated form of the amine from which diazeniumdiolates 2 are made.

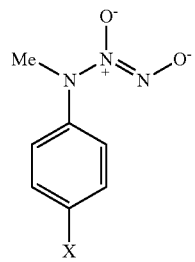

TABLE A

| X | % Amine | % NO | % Nitrosamine | % HNO | $N_2O$ ? | half-life (37° C., pH 7.4)[b] |
|---|---|---|---|---|---|---|
| H | 100 | 180 | 0 | 0 | no | 4 min |
| Cl | ≥95 | c | trace | a | a | 12 min |
| CN | 0 | 0 | 100 | 100 | yes | 11 min |
| $NO_2$ | 0 | a | 100 | c | a | a | a = not yet determined;
[b] = for comparison, the half-life of Angell's salt under these conditions is 2 min;
c = observed but not yet quantified

Example 2

In vivo cardiovascular effects obtained with HNO donor 2 (X=CN) and with its NO donor analogue 2 (X=H) in a control (normal) dog: The study was conducted in adult (25 kg) mongrel (male) dogs chronically instrumented for conscious hemodynamic analysis and blood sampling, as has been described (Katori, T.; Hoover, D. B.; Ardell, J. L.; Helm, R. H.; Belardi, D. F.; Tocchetti, C. G.; Forfia, P. R.; Kass, D. A.; Paolocci, N. *Circ. Res.* 2004, in press). Micromanometer transducers in the left ventricle provided pressure, while right atrial and descending aortic catheters provided fluid-pressures and sampling conduits. Endocardial sonomicrometers (anteriorposterior, septal-lateral) measured short-axis dimensions, a pneumatic occluder around the inferior vena cava facilitated pre-load manipulations for pressure-relation analysis. Epicardial pacing leads were placed on the right atrium, and another pair was placed on the right ventricle free wall linked to a permanent pacemaker to induce rapid pacing-cardiac failure. After 10 days of recovery, animals were evaluated at baseline sinus rhythm and with atrial pacing (120-160 bpm). Measurements included conscious hemodynamic recordings for cardiac mechanics.

Compounds were administered to a healthy control dog at the dose of 2.5 1.4/kg/min. Table B summarizes the cardiovascular data obtained. Both 2 (X=H) and 2 (X=CN) increased load-independent contractility indexes (End-systolic elastance; Ees, +25.2% and +109.6%, respectively), and reduced pre-load (end-diastolic dimension, EDD; −11.1% and −12.9%, respectively) and after-load (total resistance, RT; −24.0% and −15.1%, respectively). However, after volume loading (to rule out baroreflex discharge effects), 2 (X=H) had no effect on myocardial contractility (Ees; −14.4%), while 2 (X=CN) still enhanced contractility (Ees; +45.4%). Hence, the HNO-releasing compound 2 (X=CN) directly primes myocardial contractility. whereas the NO-releasing compound 2 (X=H) does not, in control (normal) in vivo canine myocardium.

TABLE B

| | NO Donor 2 (X=H) (2.5 μg/kg/min) | | | HNO Donor 2 (X=CN) (2.5 μg/kg/min) | | |
|---|---|---|---|---|---|---|
| | before | after | +volume loading | before | after | +volume loading |
| Ees (mmHg/mm) | 11.6 | 14.5 | 9.9 | 8.5 | 17.9 | 12.4 |
| Tau (msec) | 34.4 | 31.6 | 32.0 | 38.5 | 30.4 | 33.9 |
| LVEDD (mm) | 31.1 | 27.7 | 30.7 | 32.5 | 28.3 | 31.6 |
| LVESD (mm) | 23.6 | 20.7 | 22.3 | 23.4 | 20.0 | 21.6 |
| LVESP (mmHg) | 137.4 | 96.3 | 118.4 | 137.4 | 107.9 | 123.9 |
| LVEDP (mmHg) | 5.5 | 2.6 | 5.5 | 9.9 | 5.7 | 5.3 |
| RT (mmHg/mm/sec) | 7.3 | 5.6 | 5.6 | 6.1 | 5.2 | 5.0 |

Ees, end-systolic elastance;
Tau, relaxation time constant;
LVEDD, left ventricular end-diastolic dimension;
LVESD, left ventricular end-systolic dimension;
LVESP, left ventricular end-systolic pressure;
LVEDP, left ventricular end-diastolic pressure;
RT, total resistance.

Demonstration that 2 (X=CN) Improves Cardiac Hemodynamics in Hearts with Congestive Failure:

After completing protocols under baseline conditions, congestive heart failure was induced by tachypacing (210 bpm×3 weeks, 240 bpm×I week), as previously described (Katori, T.; Hoover, D. B.; Ardell, J. L.; Helm, R. H.; Belardi, D. F.; Tocchetti, C. G.; Forfia, P. R.; Kass, D. A.; Paolocci, N. *Circ. Res.* 2004, in press). Briefly, end-diastolic pressure and +dP/dt$_{max}$ were measured weekly to monitor failure progression. When animals demonstrated a rise in EDP>22 mmHg, and dP/dt$_{max}$ of <50% baseline, they were deemed ready for congestive heart failure studies.

Figure 6:
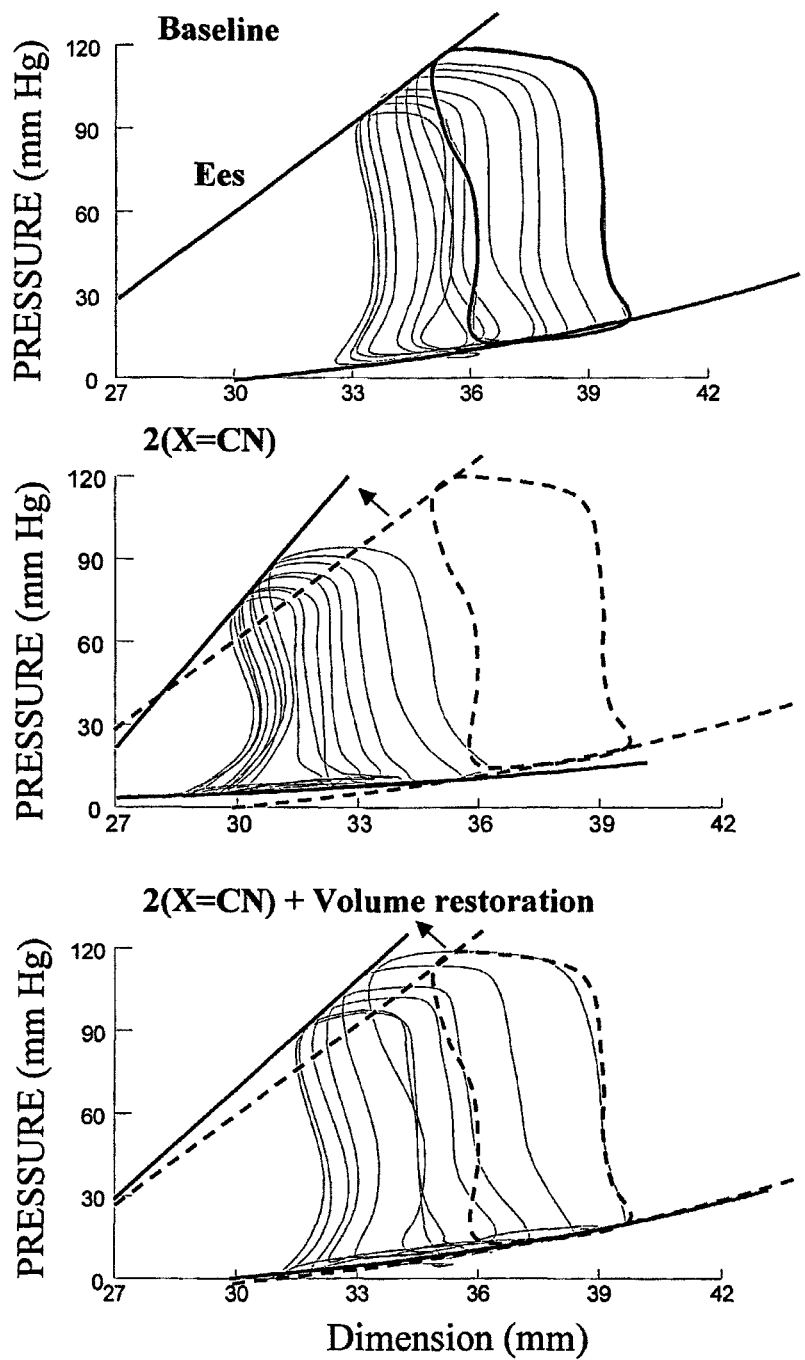
FIG. 6 illustrates the pressure-dimension loops obtained in test results on canine congestive heart failure.

FIG. 6 shows pressure-dimension loops obtained in a dog with congestive heart failure, before the administration of the HNO donor 2 (X=CN) (baseline) and after administration (2 (X=CN)). The administration of 2 (X=CN) (1.25

μg/kg/min) was accompanied by a decline in both end-diastolic dimension (EDD) and end-systolic pressure (ESP) (see also Table C), whereas the contractility index Ees was substantially enhanced as denoted by its shift to the left and higher slope. Even after volume restoration, Ees was still enhanced.

Table C compares the data obtained following administration of 2 (X═CN) in healthy control and congestive heart failure (CHF) dogs and also shows, for comparison, the data previously obtained with AS in failing dogs (Paolocci, N.; Katori, T.; Champion, H. C.; St. John, M. E.; Miranda, K. M.; Fukuto, J. M.; Wink, D. A.; Kass, D. A. *Proc. Natl. Acad. Sci. U.S.A.* 2003, 100, 5537-5542). HNO donor 2 (X═CN) reduced pre-load (LVEDD=−9.9%) and after-load (RT=−26.1%), and enhanced contractility (Ees=+70.6%) in CHF dogs. A positive inotropic effect was still observed (Ees=+33.5%) even after volume restoration, again indicating a true, primary action on the myocardium. Note that when compared to administration of the classic nitroxyl donor AS at 5-10 μg/kg/min, a much lower dose (1.25 μg/kg/min) of 2 (XN) is apparently able to elicit analogous hemodynamic effects. In addition, 2 (X═CN) appears to be very effective in reducing peripheral vascular resistance (see Table C, reduction in RT). Reduction in RT is desirable in CHF subjects who often experience persistent vascular constriction (i.e., elevated systemic vascular resistance). Therefore, 2 (X═CN) (and related analogues) may also be beneficial in this respect.

Table C also indicates that the action of 2 (X═CN) on cardiovascular function appear to be equipotent, regardless of the condition of the preparation (i.e., control vs. CHF dog). This is of particular relevance if one considers that the majority of the so-called "inotropes" (i.e., drugs that enhance myocardial contractility) lose their ability to improve myocardial function with the onset of heart failure. A good example of this phenomenon is represented by 13-adrenergic agonists, whose efficacy is largely diminished in subjects with congestive heart failure (Endoh, M. *Expert. Opin. Investig. Drugs* 2003, 12, 735-750).

Evidence that the Nitrosamine Byproduct does not Affect Cardiovascular Function:

When the nitrosamine byproduct of HNO donor 2 (X═CN) was infused alone at concentrations of 2.5 p·g/kg/min no appreciable effects either on myocardial contractility or on vascular loading conditions were observed, indicating that this byproduct is completely inactive in the cardiovascular system. The infusion of these compounds (2 (X═H), 2 (X═CN), or the corresponding nitrosamine was not followed by any overt signs of acute toxicity.

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

A number of embodiments of the invention have been described. Nevertheless, it will be understood that various modifications may be made without departing from the spirit and scope of the invention. Accordingly, other embodiments are within the scope of the following claims.

What is claimed:

1. A compound of formula (I), or a pharmaceutically acceptable salt thereof:

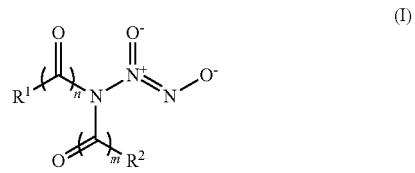

(I)

wherein:

R$^1$ and R$^2$, together with the nitrogen to which they are both attached, form a heteroaryl ring, wherein the heteroaryl ring is pyrrolyl or indolyl;

TABLE C

|  | Control Dog | | CHF Dog | | | |
| --- | --- | --- | --- | --- | --- | --- |
|  | 2 (X═CN) (2.5 μg/kg/min) | +volume loading | 2 (X═CN) (1.25 μg/kg/min) | AS (5-10 μg/kg/min) | 2 (X═CN) + volume | AS + volume |
| Ees (mmHg/mm) | +109.6% | +45.4% | +70.6% | +46 ± 8% | +33.5% | +37 ± 5% |
| Tau (msec) | −21.0% | −12.0% | −21.5% | −18 ± 2% | −19.7% | −15 ± 3% |
| LVEDD (mm) | −12.9% | −2.7% | −9.9% | −3.8 ± 1% | −2.2% | −1.7 ± 1% |
| LVESD (mm) | −14.3% | −7.4% | −11.5% | −3.9 ± 1% | −6.5% | −3.0 ± 0.5% |
| LVESP (mmHg) | −21.5% | −12.0% | −18.6% | −13 ± 2% | −4.6% | −9.9 ± 2% |
| LVEDP (mmHg) | −36.8% | −8.4% | −44.4% | −50 ± 12% | −9.2% | −34 ± 19% |
| RT (mmHg/mm/sec) | −15.1% | −18.7% | −26.1% | −12 ± 5% | −35.6% | −14 ± 4% |

All values are expressed as % from baseline. The values for 2 (X═CN) were obtained after 15 min continuous i.v. infusion (2.5 or 1.25 g/kg/min) in control and heart failure preparations, respectively, both in the absence and in the presence of volume restoration. For comparison, the same hemodynamic measurements obtained with AS (5-10 g/kg/min for 15 min i.v., n=8) in heart failure preparations are also reported.

Ees, end-systolic elastance; Tau, relaxation time constant; LVEDD, left ventricular end-diastolic dimension; LVESD, left ventricular end-systolic dimension; LVESP, left ventricular end-systolic pressure; LVEDP, left ventricular end-diastolic pressure; RT, total resistance.

wherein the heteroaryl ring is optionally substituted with from 1-4 groups selected from the group consisting of halo, COOH, NO$_2$ and ═O;

m is 0; and n is 0.

2. The compound of claim 1, or a pharmaceutically acceptable salt thereof, wherein R$^1$ and R$^2$, together with the nitrogen to which they are both attached, form a heteroaryl ring, wherein the heteroaryl ring is substituted with from 1-4 groups selected from the group consisting of halo, COOH, NO$_2$ and ═O.

3. A compound selected from the group consisting of:
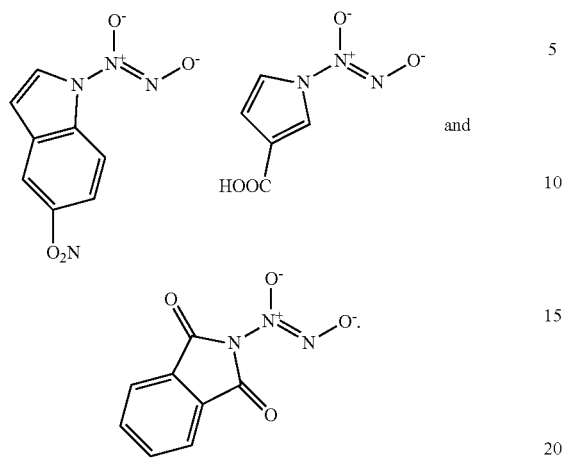
and
4. A pharmaceutical composition comprising a compound of Formula (I) in claim 1 and a pharmaceutically acceptable carrier.
* * * * *